United States Patent [19]
Miyashita et al.

[11] 4,317,821
[45] Mar. 2, 1982

[54] MAYTANSINOIDS, THEIR USE AND PHARMACEUTICAL COMPOSITIONS THEREOF

[75] Inventors: Osamu Miyashita, Osaka; Hiroshi Akimoto, Hyogo, both of Japan

[73] Assignee: Takeda Chemical Industries, Ltd., Osaka, Japan

[21] Appl. No.: 152,392

[22] Filed: May 22, 1980

[30] Foreign Application Priority Data

Jun. 8, 1979 [JP] Japan .................................. 54/72811

[51] Int. Cl.$^3$ .................... A61K 31/535; C07D 498/18
[52] U.S. Cl. .......................... 424/248.54; 260/239.3 P
[58] Field of Search ................................ 260/239.3 P; 424/248.54

[56] References Cited

U.S. PATENT DOCUMENTS 4,137,230  1/1979  Hashimoto et al. .......... 260/239.3 P

OTHER PUBLICATIONS

Kupchan et al., I "J. Am. Chem. Soc." vol. 97, No. 18, (1975) pp. 5294–5295.

Kupchan et al., II "J. Med. Chem." vol. 21, No. 1 (1978) pp. 31–37.
Higashide et al., "Nature" vol. 270 pp. 721–721 (1977).

Primary Examiner—Robert T. Bond
Attorney, Agent, or Firm—Wegner & Bretschneider

[57] ABSTRACT

Novel maytansinoids of the formula:

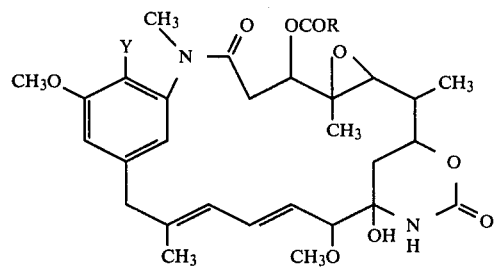

wherein Y is H or Cl, and R is $C_{2-15}$alkyl, phenyl-$C_{1-4}$alkyl, pyridyl-$C_{1-4}$alkyl, imidazolyl-$C_{1-4}$alkyl, indolyl-$C_{1-4}$alkyl, furyl-$C_{1-4}$alkyl or thienyl-$C_{1-4}$alkyl, said R group being substituted by hydroxyl, halogen or $C_{1-5}$alkanoyloxy at its $\alpha$- and/or $\beta$-position, have antimitotic, antitumor and antimicrobial activities.

12 Claims, No Drawings

MAYTANSINOIDS, THEIR USE AND PHARMACEUTICAL COMPOSITIONS THEREOF

This invention relates to novel maytansinoid compounds of the formula:

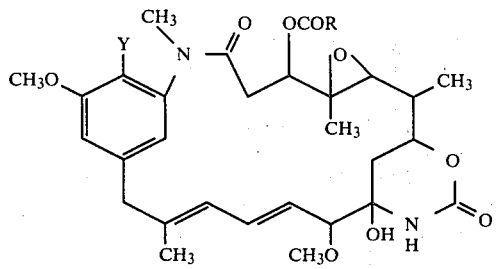

wherein Y is H or Cl, and R is $C_{2-15}$alkyl, phenyl-$C_{1-4}$alkyl, pyridyl-$C_{1-4}$alkyl, imidazolyl-$C_{1-4}$alkyl, indolyl-$C_{1-4}$alkyl, furyl-$C_{1-4}$alkyl or thienyl-$C_{1-4}$alkyl, said R group being substituted by hydroxyl, halogen or $C_{1-5}$alkanoyloxy at its α- and/or β-position, and to a method for production and use of the compounds (I).

Referring to the above formula (I), the $C_{2-15}$-alkyl group may for example be ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, neopentyl, or 2-ethylhexyl. A preferred alkyl group is $C_{2-10}$alkyl.

As examples of $C_{1-4}$alkyl moieties in the phenyl-$C_{1-4}$alkyl and heterocycle-$C_{1-4}$alkyl groups, there may be mentioned methyl, ethyl, propyl, isopropyl, butyl, isobutyl and sec-butyl, preferably methyl and ethyl. Accordingly, the phenyl-$C_{1-4}$alkyl group may for example be benzyl, phenethyl, 1-phenylethyl (α-methylbenzyl), 1- or 2-methyl-2-phenylethyl. The pyridyl-$C_{1-4}$alkyl group includes 2-, 3- or 4-pryidylmethyl and 2-(2-, 3- or 4-pyridyl)ethyl. The imidazolyl-$C_{1-4}$alkyl group includes imidazolymethyl and imidazolylethyl. The indolyl-$C_{1-4}$alkyl group includes indolylmethyl and indolylethyl. The furyl-$C_{1-4}$alkyl group includes 2- or 3-furfuryl and 2-(2- or 3-furyl)ethyl. The thienyl-$C_{1-4}$alkyl group includes 2- or 3-thienyl and 2-(2- or 3-thienyl)ethyl.

The above-mentioned $C_{2-15}$alkyl, phenyl-$C_{1-4}$alkyl and heterocycle-$C_{1-4}$alkyl groups have hydroxyl, halogen or $C_{1-5}$alkanoyloxy as a substituent or substituents at the α- and/or β-position. Said halogen atom includes chlorine, bromine, iodine and fluorine, and said $C_{1-5}$alkanoyloxy group includes formyloxy, acetyloxy, propionyloxy, butyryloxy, isobutyryloxy, pentanoyloxy and isopentanoyloxy. When both of the α- and β-positions are substituted by hydroxyls, said hydroxyls may be protected in the form of acetal. In this specification, the α-position means the adjacent carbon atom in R-groups to the carbonyl group connecting with the hydroxyl group at the 3-position of maytansinol, and the β-position means the next one to the α-position.

The groups designated by R may optionally have suitable substituents at substitutable positions, in addition to the above-mentioned substituent, i.e. hydroxyl, halogen or $C_{1-5}$alkanoyloxy at α- and/or β-position. Said substituents include $C_{1-4}$alkoxy (e.g. methoxy, ethoxy, propoxy, isopropoxy, n-butoxy, iso-butoxy, sec-butoxy, tert-butoxy), $C_{1-4}$alkanoyloxy (e.g. formyloxy, acetyloxy, propionyloxy, n-butyryloxy, isobutyryloxy), $C_{2-4}$alkoxycarbonyl (e.g. methoxycarbonyl, ethoxycarbonyl, n-propoxycarbonyl, isopropoxycarbonyl), halogen (e.g. chlorine, fluorine, bromine, iodine), nitro, cyano, trifluoromethyl, di-$C_{1-4}$alkylamino (e.g. dimethylamino, diethylamino, dipropylamino, diisopropylamino, dibutylamino), $C_{1-4}$alkylthio (e.g. methylthio, ethylthio, n-propylthio, isopropylthio, n-butylthio, isobutylthio, sec-butylthio, tert-butylthio), $C_{1-4}$alkylsulfinyl (e.g. methylsulfinyl), $C_{1-4}$alkylsulfonyl (e.g. methylsulfonyl), $C_{1-4}$alkanoylamino (e.g. formylamino, acetylamino, propionylamino, butyrylamino, isobutyrylamino), sulfamoyl and so on. When R is phenyl-$C_{1-4}$alkyl or heterocycle-$C_{1-4}$alkyl, in addition to the substituents mentioned just above, there may be mentioned, as substituents, $C_{1-4}$alkyl (e.g. methyl, ethyl, n-propyl, isopropyl, n-butyl, isobutyl, sec-butyl, tert-butyl) and $C_{2-4}$alkanoyl (e.g. acetyl, propionyl, n-butyryl, isobutyryl). These substituents may be the same or different and may total 1 to 3.

When hydroxyl, halogen or $C_{1-5}$alkanoyloxy at the α- or β-position is designated as X and the adjacent carbon atom to the carbonyl group connecting with the hydroxyl group at the 3-position of maytansinol is defined as the first (1- or α-) position, examples of the groups R may be mentioned as follows.

The relevant groups to $C_{2-15}$alkyl may for example be 1-X-ethyl, 1-X-propyl, 1-X-butyl, 1-X-isobutyl, 1-X-pentyl, 1-X-isopentyl, 1-X-hexyl, -X-octyl, 1-X-nonyl, 1-X-decyl, 1-X-undecyl, 1-X-dodecyl, 1-X-tridecyl, 1-X-pentadecyl, 1-X-1-methylethyl, 1-X-1-methylpropyl, 1-X-1-methylbutyl, 1-X-1-methylisopentyl, 2-X-ethyl, 2-X-propyl, 2-X-butyl, 2-X-1-methylbutyl, 2-X-isopropyl, 2-X-1-ethylethyl, 2-X-pentyl, 2-X-nonyl, 1,2-di-X-ethyl, 1,2-di-X-1-methylethyl and 1,2-di-X-propyl. As examples of further substituted groups, there may be mentioned 1-X-3-methylthiopropyl, 1-X-3-ethylthiopropyl, 1-X-3-methylsulfinylpropyl, 1-X-3-methylsulfonylpropyl, 1-X-2-methoxyethyl, 1-X-3-ethoxycarbonylpropyl, 1-X-2-ethoxycarbonylethyl and 2-X-3-ethoxycarbonylpropyl.

The relevant groups to phenyl-$C_{1-4}$alkyl may for example be α-X-benzyl, 1-X-2-phenylethyl, α-X-α-methylbenzyl, 1-X-1-methyl-2-phenylethyl and 2-X-1-phenylethyl. As examples of further substituted groups, there may be mentioned groups formed by replacing the phenyl in the above groups with a substituted phenyl such as 2-, 3- or 4-methylphenyl, 4-ethylphenyl, 2-, 3- or 4-chlorophenyl, 3- or 4-bromophenyl, 3- or 4-fluorophenyl, 2,4- or 3,4-dichlorophenyl, 2-, 3- or 4-methoxyphenyl, 2,5- or 3,4-dimethoxyphenyl, 4-hydroxyphenyl, 4-acetoxyphenyl, 4-butoxyphenyl, 4-iodophenyl, 3- or 4-trifluoromethylphenyl, 2- or 4-nitrophenyl, 4-cyanophenyl, 4-methanesulfonylaminophenyl, 2-chloro-4-methoxyphenyl, 2-chloro-5-methylphenyl, 2,4,6-trimethylphenyl or 3,4,5-trimethoxyphenyl.

The relevant groups to indolyl-$C_{1-4}$alkyl may for example be 1-X-1-(3-indolyl)methyl and 1-X-2-(3-indolyl)ethyl, and further substituted groups may for example be 1-X-2-(5-chloro-3-indolyl)ethyl and 1-X-2-(5-hydroxy-3-indolyl)ethyl.

The relevant groups to imidazolyl-$C_{1-4}$alkyl may for example be 1-X-2-(4(5)-imidazolyl)ethyl and 1-X-2-(1-methyl-4-imidazolyl)ethyl.

The relevant groups to furyl-$C_{1-4}$alkyl may for example be 1-X-1-(2-furyl)methyl, 1-X-1-(3-furyl)methyl, 1-X-2-(2-furyl)ethyl and 1-X-2-(3-furyl)ethyl, and further substituted groups may for example be 1-X-1-(5- methyl-2-furyl)methyl, 1-X-1-(5-methoxycarbonyl-2-furyl)methyl, 1-X-1-(5-nitro-2-furyl)methyl and 1-X-2-(5-ethoxycarbonyl-2-furyl)ethyl.

The relevant groups to thienyl-$C_{1-4}$alkyl may for example be 1-X-1-(2-thienyl)methyl, 1-X-1-(2-thienyl)ethyl, 1-X-1-(3-thienyl)methyl, 1-X-2-(2-thienyl)ethyl and 1-X-2-(3-thienyl)ethyl, and further substituted groups may for example be 3- or 5-methyl-1-X-1-(2-thienyl)ethyl and 1-X-1-(3,5-dimethyl-2-thienyl)methyl.

The relevant groups to pyridyl-$C_{1-4}$alkyl may for example be 1-X-1-(2-, 3- or 4-pyridyl)methyl, 1-X-2-(2-, 3- or 4-pyridyl)ethyl and 1,2-di-X-2-(3-pyridyl)ethyl, and further substituted groups may for example be 1-X-2-(6-methyl-2-pyridyl)ethyl and 1-X-2-(2,6-dichloro-3-pyridyl)ethyl.

The maytansinoid compound (I) of the present invention can be produced by acylating maytansinol or dechloromaytansinol of the formula:

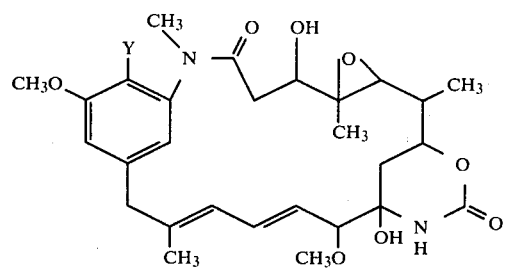

wherein Y is as defined above, with a carboxylic acid of the formula:

RCOOH                               (III)

wherein R is as defined above, or its reactive derivative with respect to the carboxyl function thereof.

An exemplary reaction procedure comprises acylating a compound (II) with a carboxylic acid (III) in the presence of a carbodiimide. Based on compound (II), carboxylic acid (III) may be used in an amount of, for example, about 1 to 50 molar equivalents and, in many cases, is preferably employed in an amount of about 1–20 molar equivalents. The carbodiimide may be used in an amount of about 1 to 70 molar equivalents based on compound (II) and, in many cases, is preferably employed in an amount of about 1–30 molar equivalents.

The usable carbodiimide is preferably dicyclohexylcarbodiimide, although such other carbodiimides may also be employed as, for example, diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

This acylation reaction may be carried out in a suitable solvent. Examples of such solvent include esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethylsulfoxide, sulfolane, etc., as well as appropriate mixtures of such solvents.

This reaction may be usually carried out at a suitable temperature from ice-cooling to the reflux point of the reaction system.

This acylation reaction can be advantageously hastened with the aid of a catalyst capable of promoting acylation of compound (II). The catalyst may be an appropriate acid or base. The basic catalyst includes, among others, tertiary amine compounds (e.g. aliphatic tertiary amines such as triethylamine; aromatic tertiary amines such as pyridine, α-, β-, or γ-picoline, 2,6-lutidine, 4-dimethylaminopyridine, 4-(1-pyrrolidinyl)pyridine, dimethylaniline, diethylaniline), halogenated alkali metals (e.g. potassium fluoride, anhydrous lithium iodide), salts of organic acids (e.g. sodium acetate) and so forth. The acid catalyst includes, among others, Lewis acids [e.g. anhydrous zinc chloride, anhydrous aluminum chloride ($AlCl_3$), anhydrous ferric chloride, titanium tetrachloride ($TiCl_4$), stannic tetrachloride ($SnCl_4$), antimony pentachloride, cobalt chloride, cupric chloride, boron trifluoride etherate, etc.], inorganic strong acids (e.g. sulfuric acid, perchloric acid, hydrochloric acid, hydrobromic acid, etc.), organic strong acids (e.g. benzenesulfonic acid, p-toluenesulfonic acid, trifluoroacetic acid, trichloroacetic acid, etc.), acidic ion exchange resins (e.g. polystyrenesulfonic acid), etc. The catalyst is used in a catalytic amount sufficient to promote acylation, for example, about 0.01 to about 10 molar equivalents, preferably about 0.01 to about 1 equivalent, based on carboxylic acid (III). The use of such a catalyst leads in many cases to remarkably improved yields of maytansinoid compound (I).

In connection with this reaction, if the carboxylic acid (III) is isomeric, i.e. D- and L-isomers, such isomers may be employed either independently or as an optional mixture. When compound (I) having an optically active acyl group is desired, the use of the corresponding optical form of carboxylic acid (III) proves advantageous in some instances. There also are cases in which even the use of an optically active carboxylic acid (III) gives rise to a mixture of D- and L-isomers of maytansinoid compound (I).

The acylation process utilizing a reactive derivative of carboxylic acid (III) with respect to its carboxyl function may for example be a process which comprises using a derivative having a functional group capable of acylating the 3-position of compound (II) such as the acid anhydride (and mixed acid anhydride cyclized through α-OH and carbonic acid) of carboxylic acid (III). The solvent and catalyst for use in this acylation reaction may be the same as those mentioned hereinbefore in connection with acylation in the presence of a carbodiimide. The reaction temperature may usually range from about −20° C. to about +100° C. and preferably about 20° C. to about 40° C. The reaction may be hastened by heating the reaction system to a still higher temperature.

In the above-mentioned acylation, when a sensitive group (e.g. hydroxyl) which reacts with the acylating agent exists in carboxylic acid (III), said group may be protected in advance by a suitable protective group [e.g. a protective group in the form of ester: lower alkanoyl (e.g. formyl, acetyl), hologenated lower alkanoyl (e.g. trifluoroacetyl, trichloroacetyl, chloroacetyl, bromoacetyl, iodoacetyl) or acyl derived from carbonic acid (e.g. tert-butyloxycarbonyl, phenoxycarbonyl); a protective group in the form of ether: benzyl, diphenylmethyl, triphenylmethyl or p-methoxybenzyl], and after the acylation, the protected compound is subjected to a reaction for removal of the protective group to obtain the contemplated compound (I).

The maytansinoid compound (I) thus produced by the above-mentioned acylation can be isolated by subjecting the reaction mixture to a conventional procedure such as concentration, solvent extraction, chromatography, recrystallization, etc. When maytansinoid compound (I) is produced as a mixture of isomers (e.g. D- and L-isomers), the isomers can be separated from each other generally by a conventional procedure, e.g. silica gel column chromatography. The maytansinoid compound (I) according to this invention includes such individual isomers and all mixtures of the isomers.

The maytansinoid compound (I) according to this invention has strong antimitotic and antitumor activities with comparatively low toxicity and are therefore suited for administration, oral or parenterally, to tumor-bearing warm-blooded animals (e.g. mouse, rat, rabbit, dog, cat and man) for the purpose of prolonging their survival times. Each compound (I) is normally administered in the form of a pharmaceutical preparation (e.g. injectable solution) as formulated with a carrier, diluent or the like which is known per se.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 μg/kg body weight, preferably about 10 to 500 μg/kg body weight, especially about 10 to 200 μg/kg body weight, per dose.

The injectable preparation can be prepared by the established pharmaceutical procedure; for example by dissolving about 50 μg to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotozoal properties. Thus, for example, the maytansinoid compounds (I) are useful for treating *tetrahymena pyriformis* w. As an antifungal or antiprotozoal agent, compound (I) is instrumental in assays of the bacterial flora of soil, active sludge, animal body fluids, etc. Thus, for the isolation of useful bacteria from soil samples or in the assay of activity of bacteria to the exclusion of those of protozoa and fungi in connection with the operation and analysis of active sludge systems for waste water treatment, the compound (I) can be advantageously employed to ensure selective growth of bacteria without permitting growth of the concomitant protozoa and fungi. Thus, such a sample is added to a liquid or solid medium, and per milliliter of the inoculated medium, 0.1 ml of a 1% methanol-water solution of about 10 to 100 μg/ml of compound (I) is added, and then incubated to let the bacteria grow and multiply.

The maytansinoid compound (I), in an amount of 0.02 ml of a 1 mg/ml aqueous solution, is able to inhibit growth of causative microorganisms of stem rot, helminthosporium leaf rot and sheath blight in rice plants, for instance, and can therefore be used for the treatment of such plant diseases. The procedure may comprise dissolving compound (I) in 1% aqueous methanol to a concentration of about 0.5 to 5 μg/ml and spraying rice plants with the solution.

The following reference example and working examples are intended to describe this invention in further detail and not to limit its scope.

REFERENCE EXAMPLE 1

In 800 ml of dry tetrahydrofuran (THF) is dissolved 15.0 g of antibiotic Ansamitocin mixture (12% of ansamitocin P-2, 71% of P-3 and 17% of P-4) and under dry nitrogen gas streams, the solution is cooled to −50° C. in a dry ice-acetone bath. Then, 13.0 g of lithium aluminum hydride (LAH) is added in a single dose and the mixture is stirred at −50° C. to −22° C. for 2 hours. Then, at −28° C., a further 3 g of LAH is added and the reaction mixture is stirred at −28° C. to −22° C. for 80 minutes. Thereafter, at −50° C., 750 ml of 2 N HCl is added dropwise with caution and the reaction mixture is extracted three times with 2.6 l, 1.6 l and 0.8 l portions of ethyl acetate. The extracts are pooled, washed with a saturated aqueous solution of sodium chloride (100 ml×2) and dried (MgSO$_4$, 250 g). The solvent is distilled off under reduced pressure and the residue (13.6 g) is chromatographed on a column of silica gel (1.2 kg), elution being carried out with ethyl acetate-water (98.5: 1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroform-hexane to obtain 0.71 g of dechloromaytansinol. m.p. 174°–179° C. (decompn.)

NMR spectrum (CDCl$_3$) δ ppm: 0.86(3H, s), 1.27(3H, d, J=ca. 6 Hz), 1.65(3H, s), 2.63(1H, d, J=9 Hz), 9.07(1H, d, J=13 Hz), 3.23(3H, s), 3.35(3H, s), 3.42(1H, d, J=13 Hz), 3.75(1H, d, J=9 Hz), 3.81(3H, s), 4.37(1H, m), 5.51(1H, dd, J=9 Hz and 15 Hz), 6.10(1H, d, J=11 Hz), 6.41(1H, dd, J=11 Hz and 15 Hz), 6.56(1H, d, J=2 Hz), 6.60(1H, s), 6.70(1H, approx. s), 6.97(1H, approx. s), Mass spectrum (m/e): 469, etc.

UV spectrum ($\lambda_{max}^{MeOH}$)nm: 231.5, 241.5, 250.5, 277.5, 286

EXAMPLE 1

In 10 ml of dry dichloromethane are dissolved 56.4 mg of maytansinol, 144.8 mg of O-trifluoroacetyl-DL-mandelic acid, 123.6 mg of dicyclohexylcarbodiimide (DCC) and 25.4 mg of 4-dimethylaminopyridine (DMAP), and the solution is stirred at room temperature. After the reaction is completed, 1 ml of a saturated aqueous solution of sodium hydrogen carbonate is added and the mixture is stirred at room temperature for about 30 minutes. The organic layer is separated and the water layer extracted twice with 5 ml portions of chloroform. The organic layers are combined and dried. Then, the solvent is distilled off under reduced pressure, and the residue is fractionated and purified by silica gel column chromatography. By this procedure are obtained two diastereoisomers of maytansinol 3-α-hydroxyphenylacetate with repsect to the center of asymmetry in the mandelic ester moiety. Fraction I (24 mg, first-emerging fraction); Fraction II (9 mg, later-emerging fraction). TLC (silica gel; Merck, HPTLC) (solvent: $CHCl_3$—MeOH=95:5): Fraction I, $R_f$=0.44; Fraction II, $R_f$=0.31. Mass spectrum (m/e): Fraction I, 637 ($M^+$-61), 485; Fraction II, 637 ($M^+$-61), 485.

EXAMPLE 2

As in Example 1, 200 mg of maytansinol, 306 mg of 2,2-dimethyl-1,3-dioxolan-4-carboxylic acid, 438 mg of DCC and 90 mg of DMAP are reacted in 15 ml of dry dichloromethane. The reaction mixture is chromatographed on a column of silica gel using a solvent mixture of chloroform-methanol (50:1). This procedure yields two diastereoisomers, with respect to the center of asymmetry in the side chain of maytansinol 3-(2,2-dimethyl)-1,3-dioxolan-4-carboxylate. Fraction I (111 mg, first-emerging fraction); Fraction II (30 mg. later-emerging fraction). TLC (silica gel, Merck, HPTLC): Fraction I, $R_f$=0.53; Fraction II, $R_f$=0.46 (solvent: chloroform-methanol=95:5).

Mass spectrum (m/e); Fraction I, 631 ($M^+$-61), 616, 485; Fraction II, 631 ($M^+$-61), 616.

EXAMPLE 3

Of the two diastereoisomers of maytansinol 3-(2,2-dimethyl)-1,3-dioxolan-4-carboxylate obtainable from maytansinol and 2,2-dimethyl-1,3-dioxolan-4-carboxylate, the fraction having a higher $R_f$ value (Fraction I) on TLC (silica gel, Merck, HPTLC; solvent: chloroform-methanol=95:5) is taken and a 84 mg portion thereof is heated in 2 ml of 70% aqueous acetic acid at 60° C. for about 10 hours. The reaction mixture is concentrated to dryness under reduced pressure and the residue is chromatographed on a silica gel column (solvent: acetonitrile-water=95:5). By this procedure is obtained 70 mg of maytansinol 3-(2,3-dihydroxy)propionate (one of diastereoisomers). Silica gel TLC (Merck, HPTLC): $R_f$=0.50 (solvent=acetonitrile-water=95:5); Mass spectrum (m/e): 591 ($M^+$-61), 576, 503.

By the same procedure as above, 16 mg of the fraction having a lower $R_f$ value (Fraction II) was reacted and treated to obtain 8 mg of maytansinol 3-(2,3-dihydroxy) propionate (the other diastereoisomer). Silica gel TLC (Merck, HPTLC): $R_f$=0.42 (solvent: acetonitrile-water=95:5). Mass spectrum (m/e): 591 ($M^+$-61), 576, 503.

EXAMPLE 4

In 5 ml of dry dichloromethane are dissolved 108 mg of maytansinol, 257 mg of L-O acetylmandelic acid and 241 mg of DCC and the mixture is stirred at room temperature for about 10 minutes. Then, 48.7 mg of DMAP is added and stirred at room temperature for an hour. The insolubles are filtered off, the filtrate concentrated to dryness under reduced pressure and the residue dissolved in ethyl acetate. The solution is washed with 1 N-hydrochloric acid, water, saturated aqueous sodium hydrogen carbonate and water in the order mentioned. The organic layer is taken and dried (over $Na_2SO_4$) and the solvent is distilled off under reduced pressure. The residue is chromatographed on 75 g silica gel (solvent: ethyl acetate) and the eluate is collected in 15-gram fractions. Fractions 31 through 48 are combined and evaporated, whereby 28.5 mg of maytansinol 3-(α-acetoxyphenyl)acetate, which is considered to be one of diastereoisomers with respect to the center of asymmetry in the side chain, is obtained as a white solid.

m.p. 177°–181° C. (decompn.) (as recrystallized from ethyl acetate-ether)

UV spectrum ($\lambda_{max}^{MeOH}$ (nm): 233, 241 (sh), 281.5, 289.5

Mass spectrum (m/e): 679 ($M^+$-61)

EXAMPLE 5

In 5 ml of dry dichloromethane are dissolved 100 mg of maytansinol, 221 mg of DL-O-acetyltropic acid and 255 mg of DCC and the mixture is stirred at room temperature. After about 5 minutes, 64.8 mg of DMAP is added and stirred at room temperature overnight. The insolubles are filtered off and the dichloromethane layer is washed with 1 N HCl, a saturated aqueous solution of sodium hydrogen carbonate and water in the order mentioned, followed by drying over $Na_2SO_4$. The solvent is then distilled off, the residue dissolved in ethyl acetate and the insolubles filtered off. The filtrate is chromatographed on silica gel (30 g) (solvent=ethyl acetate: water-saturated ethyl acetate=3:1, v/v) and the eluate is collected in 15-gram fractions. Fractions 9 through 13 are combined and evaporated, and the residue rechromatographed on silica gel (30 g) (solvent=chloroform-methanol=40:1, v/v), the eluate being collected in 25-gram fractions. Fractions 5 through 8 are combined and evaporated to give 9.8 mg of maytansinol 3-α-acetoxymethylphenylacetate (one of isomers).

UV spectrum ($\lambda_{max}^{MeOH}$ (nm)): 232, 242.5(sh), 252, 281, 290;

Mass spectrum (m/e): 693

In the first chromatographic run mentioned above, fractions 14 through 21 are combined and evaporated to give 12.6 mg of maytansinol 3-α-acetoxymethylphenylacetate.

UV spectrum ($\lambda_{max}^{MeOH}$ (nm)): 233, 242(sh), 252.5, 281, 289;

Mass spectrum (m/e): 693

EXAMPLE 6

As in Example 1, 130 mg of maytansinol, as a starting material, 235.8 mg of α-chlorophenylacetic acid, 61.2 mg of DMAP and 284.9 mg of DCC are reacted in 15 ml of dry dichloromethane. After the reaction has been completed, the dicyclohexylurea is filtered off and the filtrate is purified by silica gel column chromatography (ethyl acetate:water-saturated ethyl acetate=9:1). By this procedure are obtained two diastereoisomers of maytansinol 3-α-chlorophenylacetate with respect to the α-chlorophenylacetate moiety. Fraction I (23 mg, first-emerging fraction), Fraction II (35 mg, later-emerging fraction). Silica gel TLC (Merck, HPTLC; developing solvent: chloroform-methanol=95:5): Fraction I, $R_f$=0.67; Fraction II, $R_f$=0.59. Mass spectrum (m/e): Fraction I, 655 ($M^+$-61); Fraction II, 655 ($M^+$-61).

EXAMPLE 7

In 5 ml of dichloromethane are dissolved 53.4 mg of dechloromaytansinol, 135 mg of O-acetyl-D-mandelic acid and 129 mg of DCC and the mixture is stirred at room temperature for 5 minutes. Then, 44 mg of DMAP is added and the mixture stirred at room temperature for an hour. The insolubles are filtered off, the filtrate concentrated to dryness under reduced pressure and the residue extracted with ethyl acetate. The extract is fractionally purified by silica gel chromatography (silica gel 45 g; solvent=ethyl acetate: $H_2O$-saturated ethyl acetate=6:1, v/v). By the above procedure is obtained 15.2 mg of dechloromaytansinol 3-α-acetoxyphenylacetate (which is considered to be one of diastereoisomers with respect to the center of asymmetry in the side chain). Silica gel TLC (Merck, HPTLC; solvent: ethyl acetate): $R_f=0.29$. Mass spectrum (m/e); 645 (M+-61).

EXPERIMENTAL DATE

Antitumor activity

Therapeutic tests were carried out in mice according to NCI-protocol 1,300, Cancer Chemother, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
|---|---|---|
| Maytansinol 3-α-acetoxyphenylacetate | 12.5 | 161 |
|  | 6.25 | 260 |
|  | 3.125 | 181 |
| Maytansinol 3-α-hydroxyphenylacetate (Fraction I) | 800 | 217 |
|  | 400 | 247 |
|  | 200 | 208 |
|  | 100 | 178 |

Antiprotozoal activity

Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) *Tetrahymena pyriformis* W |
|---|---|
| Maytansinol 3-α-acetoxyphenylacetate | <2 |
| Maytansinol 3-α-acetoxymethyl-phenylacetate (from fractions 9-13 of the 1st chromatography) | 1-2 |

Examples of Pharmaceutical Compositions

Example A

Composition for Injection

| (1) Maytansinol 3-α-acetoxyphenylacetate | 50 mg |
|---|---|
| (2) Ethanol | 10 g |
| (3) Polysorbate 80 (Tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Example B

Composition for Injection

| (1) Maytansinol 3-α-hydroxyphenylacetate (Fraction I) | 200 mg |
|---|---|
| (2) Ethanol | 5 g |
| (3) Polysorbate 80 (Tween 80) | 100 g |
| (4) Mannitol | 20 g |
| (5) Distilled water, a sufficient quantity to make | 1000 ml |

Preparation

By a similar procedure to that of Example A, an injectable solution of (1) is prepared.

What we claim is:

1. A compound of the formula:

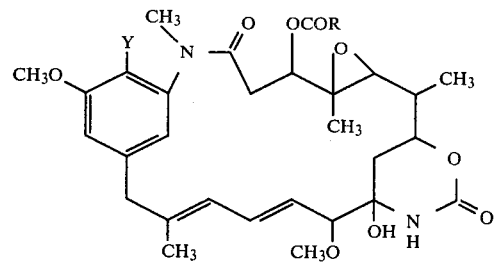

wherein Y is H or Cl, and R is phenyl-$C_{1-4}$alkyl, pyridyl-$C_{1-4}$alkyl, imidazolyl-$C_{1-4}$alkyl, indolyl-$C_{1-4}$alkyl, furyl-$C_{1-4}$alkyl or thienyl-$C_{1-4}$alkyl, each of said groups being substituted at either or both α- and β-positions by hydroxyl, halogen or $C_{1-5}$alkanoyloxy.

2. A compound according to claim 1, wherein Y is Cl.

3. A compound according to claim 1, wherein R is phenyl-$C_{1-4}$alkyl substituted at its α-position by hydroxyl, halogen or $C_{1-5}$alkanoyloxy.

4. The compound according to claim 1, which is maytansinol 3-α-hydroxyphenylacetate.

5. The compound according to claim 1, which is maytansinol 3-α-acetoxyphenylacetate.

6. The compound according to claim 1, which is maytansinol 3-α-acetoxymethylphenylacetate.

7. The compound according to claim 1, which is maytansinol 3-α-chlorophenylacetate.

8. The compound according to claim 1, which is dechloromaytansinol 3-α-acetoxyphenylacetate.

9. Maytansinol 3-(2,2-dimethyl)-1,3-dioxolan-4-carboxylate.

10. Maytansinol 3-α-acetoxyphenylacetate.

11. A pharmaceutical composition for inhibiting the growth of tumor cells and prolonging the survival time of a tumor-bearing warm-blooded animal which comprises as an active ingredient an effective amount of a compound of the formula:

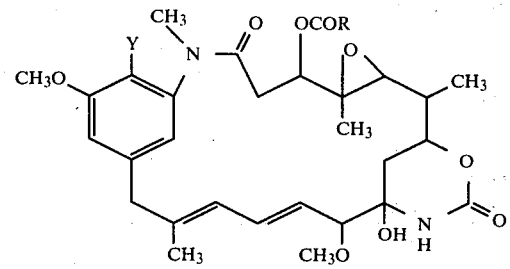

wherein Y is H or Cl, and R is phenyl-$C_{1-4}$alkyl, pyridyl-$C_{1-4}$alkyl, imidazolyl-$C_{1-4}$alkyl, indolyl-$C_{1-4}$alkyl, furyl-$C_{1-4}$alkyl or thienyl-$C_{1-4}$alkyl, each of said groups being substituted at either or both α- and β-positions by hydroxyl, halogen or $C_{1-5}$alkanoyloxy.

12. A method for inhibiting the growth of tumor cells and prolonging the survival time of a tumor-bearing warm-blooded animal which comprises administering to said animal an effective amount of a compound of the formula:

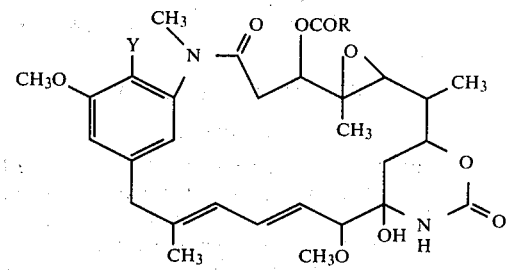

wherein Y is H or Cl, and R is phenyl-$C_{1-4}$alkyl, pyridyl-$C_{1-4}$alkyl, imidazolyl-$C_{1-4}$alkyl, indolyl-$C_{1-4}$alkyl, furyl-$C_{1-4}$alkyl or thienyl-$C_{1-4}$alkyl, each of said groups being substituted at either or both α- and β-positions by hydroxyl, halogen or $C_{1-5}$alkanoyloxy.

* * * * *